(12) United States Patent
Altshuler (10) Patent No.: US 11,796,741 B2
(45) Date of Patent: Oct. 24, 2023

(54) FIBER OPTIC ROTARY JOINT EMPLOYING HOLLOW SHAFT MOTOR

(71) Applicant: CANON U.S.A., INC., Melville, NY (US)

(72) Inventor: Alexander Altshuler, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 0 days.

(21) Appl. No.: 17/338,141

(22) Filed: Jun. 3, 2021

(65) Prior Publication Data
US 2022/0390682 A1 Dec. 8, 2022

(51) Int. Cl.
G02B 6/36 (2006.01)
G02B 6/26 (2006.01)
G02B 6/32 (2006.01)
A61B 5/00 (2006.01)

(52) U.S. Cl.
CPC ........... *G02B 6/3604* (2013.01); *G02B 6/262* (2013.01); *G02B 6/32* (2013.01); *A61B 5/0084* (2013.01)

(58) Field of Classification Search
None
See application file for complete search history.

(56) References Cited

U.S. PATENT DOCUMENTS

| | | | |
|---|---|---|---|
| 7,382,949 B2 | 6/2008 | Bouma et al. | |
| 9,345,398 B2 | 5/2016 | Tachibana et al. | |
| 9,360,630 B2 | 6/2016 | Jenner et al. | |
| 9,387,305 B2* | 7/2016 | Courtney | A61M 39/223 |
| 9,869,821 B2* | 1/2018 | Yamazaki | G02B 6/3624 |
| 10,558,001 B2 | 2/2020 | Altshuler et al. | |
| 10,962,722 B2* | 3/2021 | Popp | G02B 6/3604 |
| 11,502,633 B2* | 11/2022 | Elmaanaoui | H02P 6/22 |
| 2016/0341545 A1 | 11/2016 | Yamazaki et al. | |
| 2021/0011222 A1* | 1/2021 | Casalino | B23K 26/70 |

FOREIGN PATENT DOCUMENTS

| | | | |
|---|---|---|---|
| CN | 104793296 A | * | 7/2015 |
| JP | 2008-521022 A | | 6/2008 |
| JP | 2009-098112 A | | 5/2009 |
| JP | 2015-029567 A | | 2/2015 |
| JP | 2020-506425 A | | 2/2020 |
| KR | 20180138378 A | | 12/2018 |
| WO | 2018/003097 A1 | | 1/2018 |

* cited by examiner

*Primary Examiner* — Rhonda S Peace
(74) *Attorney, Agent, or Firm* — Canon U.S.A., Inc., IP Division (57) ABSTRACT

A fiber optics rotary joint (FORJ) connects a system console to a probe having a rotatable core, and transfers rotational motion to the probe core. The FORJ comprises a stationary optical fiber in optical communication with a rotatable optical fiber, a motor having a hollow shaft, and a fiber connector attached to a distal end of the hollow shaft. The motor is configured to rotate the rotatable optical fiber relative to the stationary optical fiber. The rotatable fiber is attached to the proximal end of the hallow shaft and connected to the fiber connector. The distal end of the stationary optical fiber is directly opposed to and aligned with the proximal end of the rotatable optical fiber such that optical axes of the stationary and rotatable optical fibers are substantially collinear with the rotational axis of the motor. The fiber connector transfers optical power and torque to the probe core.

12 Claims, 4 Drawing Sheets

FIBER OPTIC ROTARY JOINT EMPLOYING HOLLOW SHAFT MOTOR

CROSS-REFERENCE TO RELATED APPLICATIONS n/a

BACKGROUND INFORMATION

Field of Disclosure

The present disclosure generally relates to medical devices. More particularly, the disclosure is directed to a novel fiber optic rotary junction (FORJ) applicable for use in medical probes, such as endoscopes, catheters, and the like.

Description of Related Art

In minimally invasive procedures, light can be guided through a light pipe or an optical waveguide such as an optic fiber to a target to obtain optical images, perform optical measurements, conduct a medical examination, or preform therapy procedures. These and other procedures require the use of a mechanically rotated optical probe (e.g., an endoscope, catheter, or the like) inserted through a bodily lumen (e.g., blood vessel or bronchus) to reach the target. In most of these applications in order to provide reasonable field of view it is necessary to rotate the probing fiber. In order to provide continuous light transmission between the rotating probing fiber housed in a catheter, endoscope, or the like and a stationary system containing a light source and a light detector a special unit conventionally called Fiber Optic Rotary Joint (FORJ, rotary junction, or rotary joint) is usually employed. A FORJ must provide mechanical actuation and optical connectivity between the optical probe and an operating console. The optical connection allows the optical system to communicate with the rotating distal end of the probe, and the mechanical connection allows the optical probe to rotate or oscillate to scan the bodily lumen. To reduce positional accuracy requirements at the FORJ some beam expansion means (such as collimators) are generally used for beam transmission in a gap between stationary and rotating fibers. In some applications, the FORJ also includes a translation stage to mechanically displace the optical probe in a lengthwise direction along the lumen. To reduce positional accuracy requirements at the FORJ some beam expansion components (such as collimators) are generally used for beam transmission in a gap between stationary and rotating fibers.

A fiber optic rotary joint can be implemented in various manners. However, regardless of how the rotary joint is implemented, a motor (e.g., a DC motor, stepping motor, or the like) is necessary to drive the rotation of the optical probe. The motor and other mechanical, optical, and electronic components of the rotary junction are enclosed in a patient interface module or patient interface unit (PIU). One example of a rotary joint is described in U.S. Pat. No. 7,382,949. Also, U.S. Pat. Nos. 9,360,630 and 9,345,398 describe more examples of known driving assemblies for a rotary junction. These and other U.S. patents and patent application publications are incorporated by reference herein for all purposes.

Conventional rotary joints of the type described in the above-referenced patents tend to use of large, cumbersome, and expensive components which renders the overall system less efficient than desired. For example, the rotary joint described in U.S. Pat. Nos. 7,382,949 and 9,345,398 uses a rotary motor which drives the rotating portion of the FORJ through a timing belt or gear. This results in a mechanically complex unit with a large number of components and increased mechanical vibrations. The FORJ disclosed in U.S. Pat. No. 9,360,630 uses a hollow shaft motor where the optical signal is transmitted through a hollow shaft from a stationary collimator to a rotating collimator. In this patent, the relatively large gap (distance) between two collimators makes the FORJ very sensitive to component misalignment and mechanical vibrations. In addition, having the rotating collimator on the disposable catheter makes the disposable part of the system more expensive.

Therefore, there remains a need for improved fiber optic rotary joints applicable for use in medical probes, such as endoscopes, catheters, and the like.

SUMMARY OF EXEMPLARY EMBODIMENTS

According to at least one aspect, the present disclosure is directed to a fiber optics rotary joint (FORJ) which connects a system console to a probe having a rotatable core, and transfers rotational motion to the probe core. The FORJ comprises a stationary optical fiber in optical communication with a rotatable optical fiber, a motor having a hollow shaft, and a fiber connector attached to a distal end of the hollow shaft. The motor is configured to rotate the rotatable optical fiber relative to the stationary optical fiber. The rotatable fiber is attached to the proximal end of the hallow shaft and connected to the fiber connector. The distal end of the stationary optical fiber is directly opposed to and aligned with the proximal end of the rotatable optical fiber such that optical axes of the stationary and rotatable optical fibers are substantially collinear with the rotational axis of the motor. The fiber connector transfers optical power and torque to the probe core.

According to another aspect, the present disclosure is directed to a method of providing optical communication between a system console and a probe having a rotatable probe core, and imparting rotational motion on the probe core. The method comprising: arranging a first optical system having a stationary optical fiber in communication with the system console, the stationary optical fiber having a distal end; arranging a second optical system comprising a rotatable optical fiber relative to the first optical system, the rotatable optical fiber having a proximal end and a distal end; providing a motor comprising a hollow shaft which spans from a proximal end to a distal end along a rotational axis of the motor; and affixing an optical fiber connector at the distal end of the hollow shaft, the optical fiber connector adapted to connect to the rotatable probe core; wherein the rotatable optical fiber is affixed to the proximal end of the hollow shaft and is connected to the optical fiber connector at the distal end of the hollow shaft, wherein the distal end of the stationary optical fiber is arranged directly opposed to and aligned with the proximal end of the rotatable optical fiber with a gap therebetween such that an optical axis of the stationary optical fiber and an optical axis of the rotatable optical fiber and the rotational axis of the motor are substantially collinear, and wherein imparting rotational motion on the probe core includes rotating the rotatable optical fiber about the rotational axis with the motor and transferring the rotational motion to the probe core via optical fiber connector.

These and other aspects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

DETAILED DESCRIPTION OF EXEMPLARY EMBODIMENTS

Before the various embodiments are described in further detail, it is to be understood that the present disclosure is not limited to any particular embodiment. It is also to be understood that the terminology used herein is for the purpose of describing exemplary embodiments only, and is not intended to be limiting.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those skilled in the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation to expressly exclude a feature or step or component.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to be inclusive of end values and includes all sub-ranges subsumed therein, unless specifically stated otherwise. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

Unless specifically stated otherwise, as apparent from the following disclosure, it is understood that, throughout the disclosure, discussions using terms such as "processing," "computing," "calculating," "determining," "displaying," or the like, refer to the action and processes of a computer system, or similar electronic computing device, or data processing device that manipulates and transforms data represented as physical (electronic) quantities within the computer system's registers and memories into other data similarly represented as physical quantities within the computer system memories or registers or other such information storage, transmission or display devices. Computer or electronic operations described in the specification or recited in the appended claims may generally be performed in any order, unless context dictates otherwise. Also, although various operational flow diagrams are presented in a sequence(s), it should be understood that the various operations may be performed in other orders than those which are illustrated or claimed, or operations may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "in response to", "related to," "based on", or other like past-tense adjectives are generally not intended to exclude such variants, unless context dictates otherwise.

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their state in a three-dimensional space. As used herein, the term "position" refers to the location of an object or a portion of an object in a three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to six total degrees of freedom); the term "shape" refers to a set of posture, positions, and/or orientations measured along the elongated body of the object.

As it is known in the field of medical devices, the terms "proximal" and "distal" are used with reference to the manipulation of an end of an instrument extending from the user to a surgical or diagnostic site. In this regard, the term "proximal" refers to the portion (e.g., a handle) of the instrument closer to the user, and the term "distal" refers to the portion (tip) of the instrument further away from the user and closer to a surgical or diagnostic target site. It will be further appreciated that, for convenience and clarity, spatial terms such as "vertical", "horizontal", "up", and "down" may be used herein with respect to the drawings. However, imaging and/or surgical instruments are used in many orientations and positions, and these terms are not intended to be limiting and/or absolute.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

In the present disclosure, the terms "optical fiber", "fiber optic", or simply "fiber" refers to an elongated, flexible, light conducting conduit (a waveguide) capable of conducting light from one end to another end due to the effect known as total internal reflection. The terms "light guiding component" or "waveguide" or "light pipe" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding or multiple claddings. The refraction index of the core is larger than the refraction index of the cladding or claddings.

The following disclosure is directed to a novel fiber optic rotary junction (FORJ) applicable for use in medical imaging systems that use intraluminal optical probes, such as endoscopes, catheters, and the like.

Fiber Optic Rotary Joint

Figure 1:
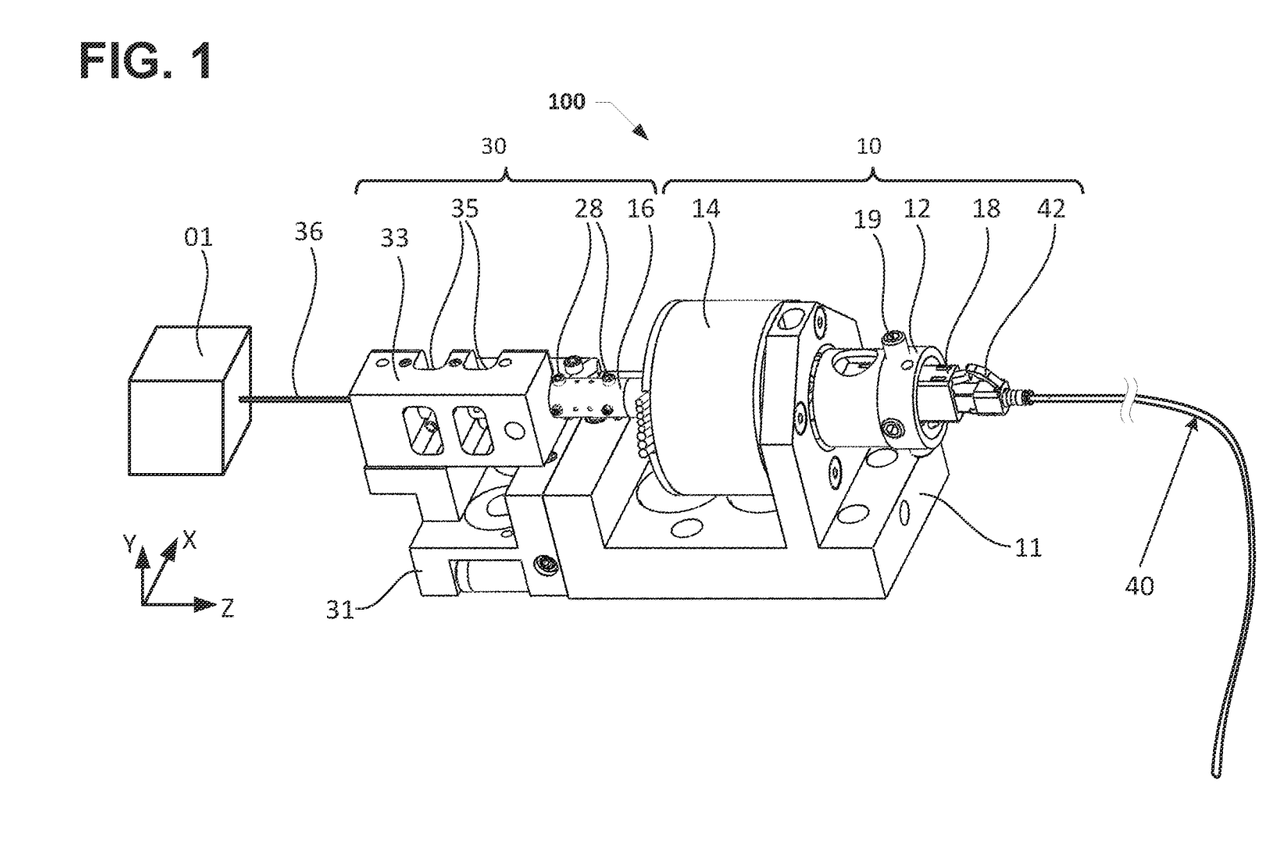
FIG. 1 shows a perspective view of a fiber optic rotary joint according to one embodiment of the present disclosure.
Figure 2:
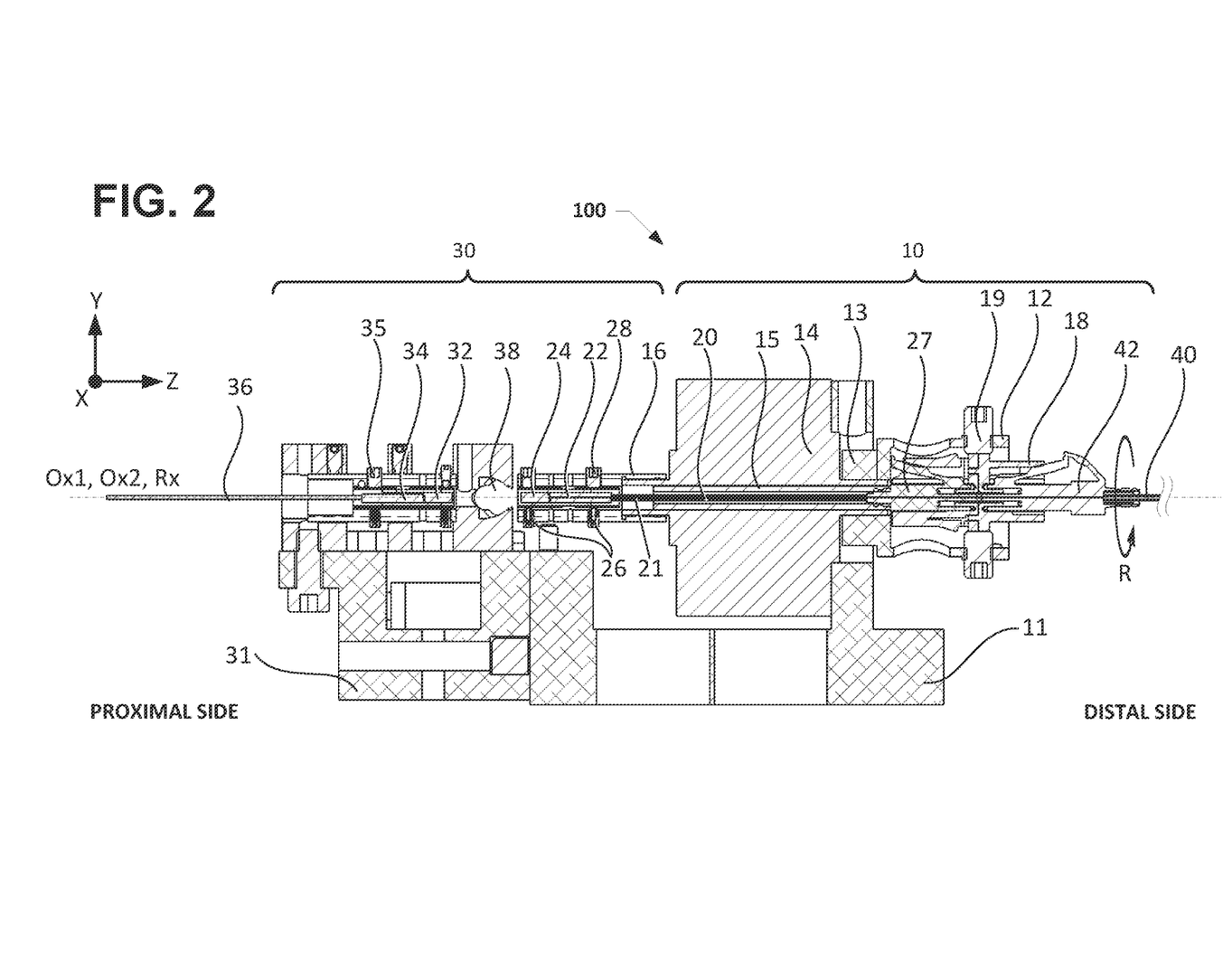
FIG. 2 shows a cross sectional view of a fiber optic rotary joint according to one embodiment of the present disclosure.

FIG. 1 shows a perspective view and FIG. 2 shows a cross sectional view of a fiber optic rotary joint 100 according to one embodiment of the present disclosure. According to this embodiment, the rotary joint 100 is comprised of a motor unit 10, a fiber assembly 20, and a stationary unit 30. The motor unit 10, fiber assembly 20, and stationary unit 30 are joined together in a manner that will allow their relative motion in X and Y directions for optical alignment purposes and then locking the alignment while maintaining a free space or gap 38 between the fiber assembly 20 and stationary unit 30. In FIG. 1 and FIG. 2, where X, Y, Z axes are perpendicular to each other, the X direction is perpendicular to the drawing plane, the Y direction is perpendicular to X (vertical in the plane of FIG. 2), and the Z direction is parallel to the drawing plane (horizontal in the plane of FIG. 2).

The stationary unit 30 is in optical communication with a system console 01 through an optical fiber 36. The system console 01 includes, among other components, a non-illustrated light source and a light detector. The non-illustrated light source and light detector can be implemented in any known manner depending on the application or applications of the imaging system. In some embodiments, the imaging system may include an optical coherence tomography (OCT) imaging system. In this case, the system may use a swept-source laser (wavelength 1310 nm+/−50 nm) as the OCT light source, and the light detector may include a balanced photodetector comprised of a photomultiplier tube (PMT), a photodiode, an avalanche photodiode detector (APD), a charge-coupled device (CCD), a multi-pixel photon counter (MPPC), or combinations thereof. The optical fiber 36 terminates in the stationary unit 30 with a ferrule 34 and a collimator lens 32. The collimator lens 32 expands a beam of light delivered by the optical fiber 36, and projects the expanded beam along an optical axis Ox1 towards the motor unit 10. The direction of the optical axis Ox1 of the stationary unit 30 may be adjusted relative to a base 31 of the stationary unit 30 by one or more alignment screws 35 provided on an adjustable stage 33.

The motor unit 10 is comprised of a motor 14 with a hollow shaft 15 having a rotational axis Rx. The motor unit 10 is mounted on a motor base 11. A rotating fiber assembly 20 is placed inside the lumen of the motor's hollow shaft 15. The fiber assembly 20 includes a fiber 21 spanning from a proximal end to a distal end along an optical axis Ox2. The fiber 21 is terminated by a ferrule 22 and a rotating collimator lens 24 on the proximal end, and by a standard LC type fiber optic connector 27 with a standard LC type adapter 18 on the distal end. The proximal end of the fiber assembly 20 is placed inside a collimator housing 16 which is rigidly affixed to the proximal end of the motor shaft 15. The collimator housing 16 is a hollow tubular body which may be glued, clamped on, or even integrally incorporated in the hollow shaft 15. That is, in some embodiments, the collimator housing 16 may be an integral part (e.g., a protruding extension) of the hollow shaft 15. The collimator housing 16 includes a plurality of fine adjustment screws 28 (four in one embodiment) backed by four counter biasing springs 26 which allow for alignment of the optical axis Ox2 of the fiber assembly 20 with the rotational axis Rx of the motor unit 10.

On the distal side of the motor unit 10, an LC connector hub 12 is rigidly affixed to the distal end of the motor shaft 15 by a clamp 13. The LC adapter 18 is firmly held inside the LC connector hub 12 by a plurality of set-screws 19 (four in one embodiment). The LC adapter 18 has a rectangular shape which allows for secure engagement to the connector hub 12, and easy torque transmission from the motor's shaft 15 to the adapter 18. In this manner, the adapter 18 can transmit rotational motion to a fiber connector 42 to rotate or oscillate a probe core 40 as shown by arrow R.

Here, the standard LC fiber optic connector and LC adapter are mentioned as an example of fiber optic connection components which are easy to plug in or remove, while providing a secure and precisely aligned fit conforming to TIA/EIA 604 standards. However, other types of standard fiber optic connection components such as SC, FC, and ST connectors can be used in a similar manner. The optical fiber 21 used in the rotating fiber assembly 20 and the optical fiber 36 used in the stationary fiber assembly 30 may be chosen from a single mode fiber, a double clad fiber, or a multimode fiber.

Alignment of Motor Rotational Axis Rx with Optical Axis Ox2 of Fiber Assembly Optical alignment of the FORJ will ensure reliable optical communication between the stationary unit 30 and the rotatable fiber assembly 20 held by motor unit 10 through an air gap 38 formed between the collimator lens 32 and the collimator lens 24. In one embodiment, the air gap 38 may be in a range of about 1.0 mm to 10.0 mm. This is a significant reduction of the gap size as compared to conventional rotary joints where the air gap typically has to additionally include the length of the hollow shaft of the motor. In some embodiments, the gap 38 formed between the collimator lens 32 and the collimator lens 24 can be filled with an optical coupling fluid (e.g., liquid, gel, or gas) to enhance optical transmission therebetween.

Optical alignment of the non-rotating components, the rotatable fiber assembly, and the motor unit 10 can be accomplished in a known manner as it is known to persons having ordinary skill in the art. For example, the overall optical alignment may include plural steps. In a first step, the optical axis Ox2 of the fiber assembly 20 is caused to be aligned coincident with the axis of rotation Rx of the motor unit 10. More specifically, the optical axis Ox2 of the fiber assembly 20 arranged in the lumen of hollow shaft 15 should be aligned with the axis of rotation Rx of the motor 14. In a second step, the optical axis Ox1 of the optical components in the stationary unit 30 is caused to be at the same angle as the aligned axis of rotation Rx of motor unit 10. In this step, the optical axis Ox1 of the non-rotating optical components in the stationary unit 30 should be aligned substantially coincident with Z axis direction, by operating the one or more alignment screws 35. After the two steps, the two optical axes of the two optical components (stationary unit 30 and motor unit 10) have been aligned to be parallel with each other. Therefore, only horizontal and vertical translational alignments need to be performed. This is performed in a third step. In the third step, the collimator 32 and the collimator 24 are brought to directly face each other to allow only sliding motion in the X and Y directions between them. Thereafter, a sliding motion between the facing surfaces of the collimator 32 and collimator 24 is performed until the optical axis Ox1 of the stationary unit 30, the optical axis Ox2 of the fiber assembly 20, and the rotational axis Rx of motor unit 30 are substantially collinear. As used herein, the term "collinear" is given its ordinary geometrical meaning whereby three or more points are said to be collinear if they lie on a single straight line. At the end of the third step, the entire optical alignment of the FORJ assembly 100 is completed. A detailed procedure for this type of optical alignment is described in the inventor's previously published U.S. Pat. No. 10,558,001 A1 which is incorporated by reference herein for all purposes.

Figure 3A:
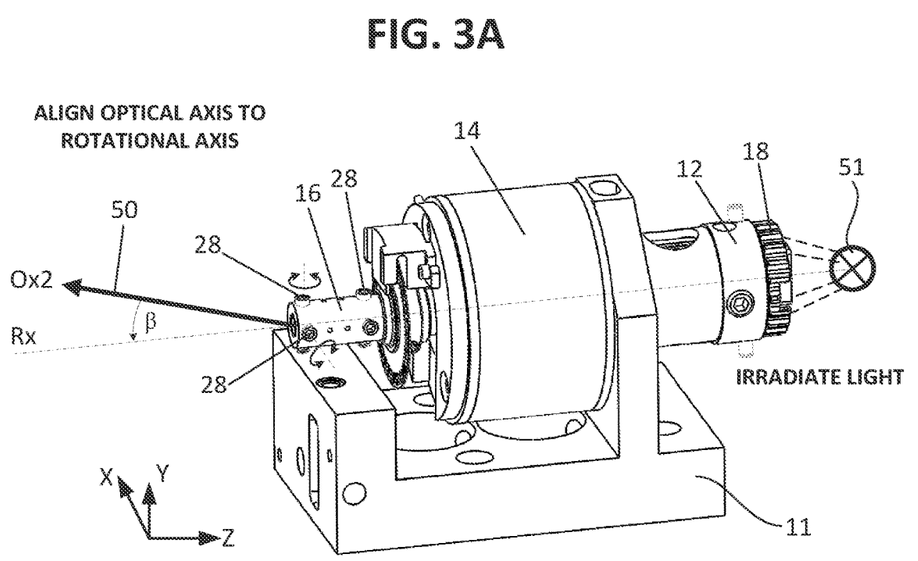
FIG. 3A and FIG. 3B show perspective views of the FORJ to explain a process of aligning the optical axis Ox2 of the fiber assembly 20 with the motor's rotational axis Rx.
Figure 3B:
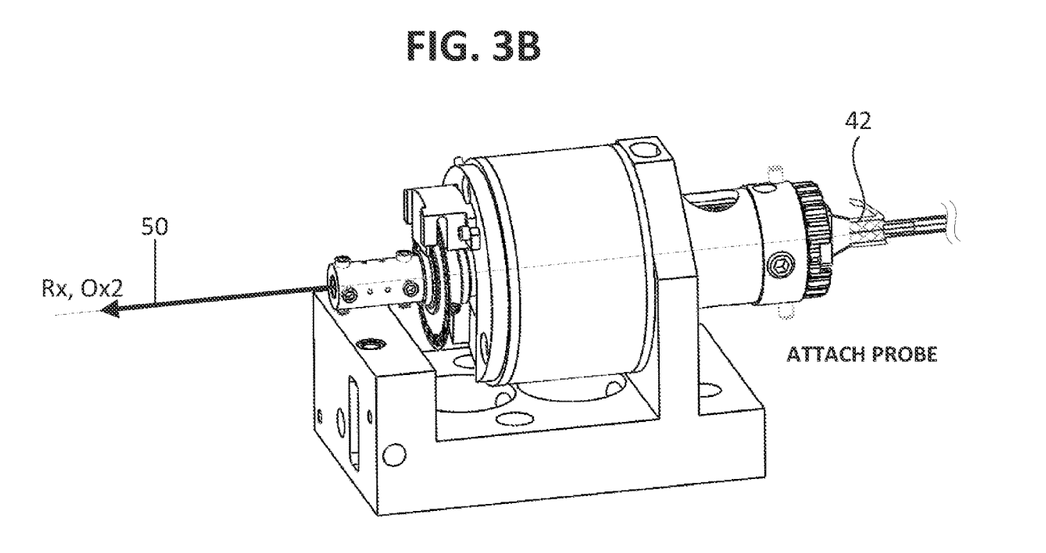

FIG. 3A and FIG. 3B show perspective views of the FORJ to explain a process of aligning the optical axis Ox2 of the fiber assembly 20 with the motor's rotational axis Rx. FIG. 3A shows a status of the optical axis Ox2 of the fiber assembly 20 with respect to the axis of rotation Rx of motor unit 10 before alignment. In this step, a beam of light 50 can be transmitted from a light source 51 though the fiber connector 18. Before alignment, the beam of light 50 exits at the proximal end of the fiber assembly 20 at an angle β with respect to the motor's rotational axis Rx. To align the optical axis Ox2 of the fiber assembly 20 with the axis of rotation Rx of motor unit 10, the user operates one or more of the set screws 28 until the beam of light 50 coincides with the rotational axis Rx. FIG. 3B shows a status where the optical axis Ox2 is aligned with the axis of rotation Rx. In the status where the beam of light 50 is aligned coincident (collinear) with the rotation axis Rx, the user can safely attach a connector 42 of an imaging probe 40 to the rotary joint. In this manner, the optical alignment of the stationary and rotatable fiber is performed once during assembly, and needs not be done every time a new probe is attached.

The motor 14 should preferably include an encoder to facilitate alignment between the FORJ and a probe's optical connector by providing predetermined FORJ connector position(s) on engagement and disengagement. Encoders are well known to persons having ordinary skill in the art. For the FORJ, an optical encoder can be a built-in encoder or an external encoder strategically arranged to provide predetermined connector position(s) on engagement and disengagement.

It should be noted that the rotating optical fiber disposed in the lumen of the hollow shaft 15 of motor 14 functions exclusively a light guide, rather than free space optics media for a collimated beam like in some prior art. The implementation of the rotating optical fiber as a light guide eases the burden of critical alignment between rotational and stationary fibers by making the alignment needed to be done just once for the non-disposable portion of the instrument while making every connection to the disposable probe not critical in terms of optical alignment.

As it can be understood by persons of ordinary skill in the art, an optical fiber uses the effect of total internal reflection for light propagation, and modern fiber optics technology allows for a fiber to be bent or linearly offset without any significant loss of light transmission between the two ends of a fiber. Therefore, in the present disclosure, for optimal coupling of light transmission, the fiber needs accurate alignment on the light entrance and exit points; this is achieved by the process illustrated in FIG. 3A-FIG. 3B. Free space optics, on the other hand, relies on light propagating in straight lines and requires very precise alignment between the light entrance and exit points. Therefore, adding a short span of fiber between the light entrance and exit points of the motor's hollow shaft advantageously reduces alignment requirements and ensures substantially lossless optical transmission.

In operation, a catheter or other intraluminal instrument having a probe core 40 is connected to the LC connector 27 by inserting another standard LC connector 42 of the probe core into the LC adapter 18. In this manner, the proximal end of the probe core 40 is optically connected to the distal end of rotating optical fiber assembly 20. Using the standard LC connector 42, which also has a square outside profile, ensures easy and reliable mechanical connection with the LC adapter 18. In addition, using standard components (standard LC adapter 18 and LC connector 42) provides proven reliable optical connections, as well as simplified rotational motion transmission between the FORJ and the probe core 40 without the need for actively confirming optical alignment between the probe core 40 and the rotating optical fiber assembly 20.

Exemplary Imaging System

Figure 4:
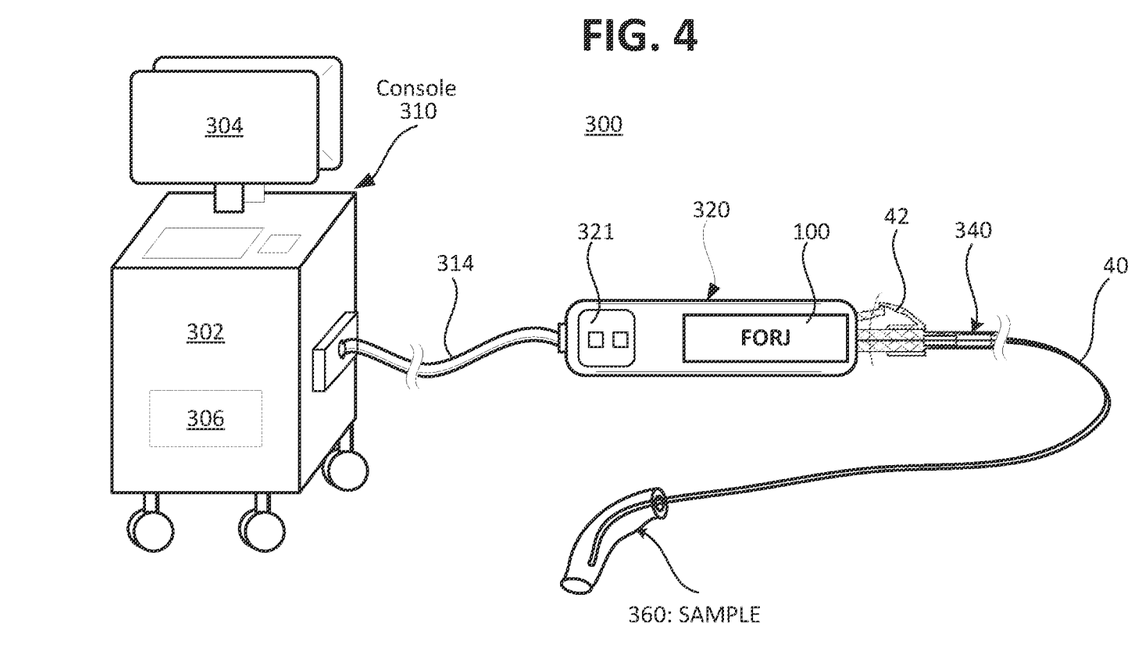
FIG. 4 illustrates an exemplary system incorporating therein a fiber optic rotary joint according to the present disclosure.

FIG. 3 illustrates an exemplary system 300 incorporating therein a fiber optic rotary joint 100 according to the present disclosure. According to one example, the FORJ 100 can be applicable to medical imaging system 300 which includes an imaging console 310 (system console) and a disposable or limited use optical probe 340 (e.g., endoscope or catheter). A patient interface unit (PIU) 320 connects the optical probe 340 to the imaging console 310 using a cable bundle 314. The imaging console 310 includes, among other things, a computer cart 302 and one or more displays 304. The computer cart 302 encloses system components 306 including at least one or more processors, one or more light sources (laser sources), and one or more light detectors, etc. The optical probe 340 may include, for example, a fiber-optic based catheter having a probe core 40. In an exemplary imaging procedure, the imaging system 300 uses the probe core 40 to obtain images of an imaging sample 360, such as a cardiovascular bodily lumen of a patient.

The PIU 320 is the main interface between the probe 340 and the system console 310. The PIU provides the means to spin and linearly translate the probe's imaging core within the catheter's stationary outer sheath. The console 310 and PIU 320 are connected by the cable bundle 314. The cable bundle 314 houses therein cables for transmitting electrical power and for communication signaling, as well as optical fibers (e.g., optical fiber 36) for light transmission. During operation of the imaging system 300, the entire PIU 320 is preferably covered with a sterile drape and placed on the patient's bed or operating table. The PIU 320 may provide a user interface for operating the imaging functions of the probe from an sterile field by the use of actionable buttons 321; these buttons 321 may mirror other controls provided on the system console 310, e.g. a graphical user interface (GUI) shown in the display 304.

The PIU 320 may include non-illustrated a beam combiner, the fiber optic rotary joint (FORJ) 100, a motion mechanism including a linear stage, electronic control boards, control buttons and/or an LED panel. As shown, the FORJ 100 is configured to receive therein a connector 42 for the probe 340.

Software Related Disclosure

At least certain aspects of the exemplary embodiments described herein can be realized by a computer of a system or apparatus that reads out and executes computer executable instructions (e.g., one or more programs or executable code) recorded on a storage medium (which may also be referred to as a 'non-transitory computer-readable storage medium') to perform functions of one or more block diagrams or flowchart diagrams described above. The computer may include various components known to a person having ordinary skill in the art. For example, the computer may include signal processor implemented by one or more circuits (e.g., a field programmable gate array (FPGA) or an application specific integrated circuit (ASIC)) for performing the functions of one or more of the above-described embodiment(s), by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)), and may include a network of separate computers or separate processors to read out and execute the computer executable instructions. The computer executable instructions may be provided to the computer, for example, from a cloud-based network or from the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. The computer may include an input/output (I/O) interface to receive and/or send communication signals (data) to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

The novel FORJ disclosed herein provides several technical advantages over conventional rotary joints known in the prior state of the art including, but not limited to:

Shorter air gap distance between stationary and rotating portions of the FORJ. This is compared to the prior art using the hollow shaft motor bore as a free-space media for light beam propagation. In that case the light should travel in air or other media (free space optics) through the entire length of the shaft, thus adding to the air gap length;

Low cost and reliable standard probe/catheter core connection. In this regard, for example, it is noted that having the standard fiber adapter 18 configured to receive the probe's fiber connector 42 alleviates the need for alignment during connection and removal of the probe;

Lower parts count which results in lower cost, higher reliability;

Lower design and assembly complexity. For example, the optical alignment of the stationary and rotatable fiber is performed once during assembly, and needs not be done every time a new probe is attached;

Less mechanical vibration effects.

Other Embodiments or Modifications

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by persons of ordinary skill in the art to which this disclosure belongs. In that regard, breadth and scope of the present disclosure is not limited by the specification or drawings, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner. Therefore, the scope of the following claims is to be accorded the broadest interpretation so as to encompass all such modifications and equivalent structures and functions.

What is claimed is:

1. A fiber optics rotary joint for providing optical communication between a stationary system and a probe having a rotatable probe core, and imparting rotational motion on the probe core, the fiber optics rotary joint comprising:
    a stationary unit comprising a stationary optical fiber assembly in communication with the stationary system, the stationary optical fiber assembly having a distal end;
    a motor unit comprising a hollow shaft motor, the hollow shaft motor having a hollow shaft with a lumen that spans from a proximal end to a distal end along a rotational axis, Z, of the hollow shaft motor;
    the motor unit and the stationary unit are joined together in a manner that will allow their relative motion in the X and Y directions, where X and Y are orthogonal to Z; and
    a rotatable optical fiber assembly having a proximal end and a distal end, the rotatable optical fiber assembly disposed inside the lumen of the hollow shaft along the rotational axis of the hollow shaft motor, and spanning between the proximal and distal ends of the hollow shaft;
    wherein:
    the rotatable optical fiber assembly further comprises an optical fiber connector affixed to the distal end of the hollow shaft and adapted to connect to a mating connector of the probe core;
    the rotatable optical fiber assembly is affixed to the proximal end of the hollow shaft; and
    the distal end of the stationary optical fiber assembly is directly spatially opposed to and adapted for optical communication with the proximal end of the rotatable optical fiber assembly.

2. The fiber optics rotary joint according to claim 1, wherein both the rotatable optical fiber assembly on its proximal end and the stationary optical fiber assembly on its distal end further comprise matching opposed collimator lenses.

3. The fiber optics rotary joint according to claim 2, wherein both the proximal end of the rotatable optical fiber assembly and the distal end of the stationary optical fiber assembly further comprise features adapted for optical alignment of the matching opposed collimator lenses.

4. The fiber optics rotary joint according to claim 3, wherein the features adapted for optical alignment are configured to move one or more of the rotatable optical fiber assembly and the stationary optical fiber assembly with respect to each other until an optical axis of the stationary optical fiber assembly and an optical axis of the rotatable optical fiber assembly and the rotational axis of the hollow shaft motor are substantially collinear.

5. The fiber optics rotary joint according to claim 1, wherein both the proximal end of the rotatable optical fiber assembly and the distal end of the stationary optical fiber assembly are adapted for direct fiber-to-fiber optical transmission via a gap therebetween.

6. The fiber optics rotary joint according to claim 5, wherein the gap establishes a distance of about 1.0 to 10.0 millimeters between the proximal end of the rotatable optical fiber assembly and the distal end of the stationary optical fiber assembly.

7. The fiber optics rotary joint according to claim 1, wherein the motor unit and the stationary unit can be locked together to prevent relative motion in the X and Y directions after alignment while maintaining a free space or gap between the fiber assembly and stationary unit.

8. An apparatus for delivering a rotating beam of light to an intraluminal target via a probe having a rotatable probe core, the apparatus comprising:
a first optical system comprising a stationary optical fiber;
a second optical system comprising a rotatable optical fiber, the rotatable optical fiber having a proximal end and a distal end;
a hollow shaft motor having a hollow shaft with a lumen that spans from a proximal end to a distal end along a rotational axis, Z, of the hollow shaft motor;
the hollow shaft motor and the first optical system unit and the stationary unit are joined together in a manner that will allow their relative motion in the X and Y directions, where X and Y are orthogonal to Z; and
an optical fiber connector affixed to the distal end of the hollow shaft, the optical fiber connector adapted to connect to the rotatable probe core;
wherein the rotatable optical fiber is affixed to the proximal end of the hollow shaft, is arranged through the lumen of the hollow shaft along the rotational axis of the hollow shaft motor, and is connected to the optical fiber connector at the distal end of the hollow shaft,
wherein the distal end of the stationary optical fiber is directly opposed to and aligned with the proximal end of the rotatable optical fiber such that an optical axis of the stationary optical fiber and an optical axis of the rotatable optical fiber and the rotational axis of the hollow shaft motor are substantially collinear, and
wherein the hollow shaft motor is configured to rotate the rotatable optical fiber about the rotational axis and the optical fiber connector transfers rotational motion to the probe core.

9. A method of providing optical communication between a system console and a probe having a rotatable probe core, and imparting rotational motion on the probe core, the method comprising:
arranging a first optical system having a stationary optical fiber in communication with the system console, the stationary optical fiber having a distal end;
arranging a second optical system comprising a rotatable optical fiber relative to the first optical system, the rotatable optical fiber having a proximal end and a distal end;
providing a hollow shaft motor having a hollow shaft with a lumen that spans from a proximal end to a distal end along a rotational axis, Z, of the hollow shaft motor;
affixing an optical fiber connector at the distal end of the hollow shaft, the optical fiber connector adapted to connect to the rotatable probe core, and
aligning the first optical system unit and the stationary unit in the X and/or Y directions, where X and Y are orthogonal to Z, by moving the first optical system and/or the hollow shaft motor relative to each other,
wherein the rotatable optical fiber is affixed to the proximal end of the hollow shaft, is arranged through the lumen of the hollow shaft along the rotational axis of the hollow shaft motor, and is connected to the optical fiber connector at the distal end of the hollow shaft,
wherein the distal end of the stationary optical fiber is arranged directly opposed to and aligned with the proximal end of the rotatable optical fiber with a gap therebetween such that an optical axis of the stationary optical fiber and an optical axis of the rotatable optical fiber and the rotational axis of the hollow shaft motor are substantially collinear, and
wherein imparting rotational motion on the probe core includes rotating the rotatable optical fiber with the hollow shaft motor such that the rotatable optical fiber rotates about the rotational axis of the hollow shaft motor, and transferring the rotational motion to the probe core via the optical fiber connector.

10. The method according to claim 9, further comprising:
providing features adapted for optical alignment of both the rotatable optical fiber assembly and the stationary optical fiber assembly.

11. The method according to claim 9, further comprising:
operating the features adapted for optical alignment to move one or more of the rotatable optical fiber assembly and the stationary optical fiber assembly with respect to each other until the optical axis of the stationary optical fiber assembly and the optical axis of the rotatable optical fiber assembly and the rotational axis of the hollow shaft motor are substantially collinear.

12. The method according to claim 9, further comprising locking the first optical system and the hollow shaft motor together to prevent relative motion in the X and Y directions after aligning the first optical system unit and the stationary unit.

* * * * *